United States Patent
Lopez et al.

(10) Patent No.: US 8,137,404 B2
(45) Date of Patent: Mar. 20, 2012

(54) ARTIFICIAL DISC REPLACEMENT USING POSTERIOR APPROACH

(75) Inventors: Erasmo Lopez, Abington, MA (US); Amie Borgstrom, North Attleboro, MA (US); SeungKyu Daniel Kwak, Grafton, MA (US); John Riley Hawkins, Cumberland, RI (US); Charles M. Bartish, Jr., Providence, RI (US)

(73) Assignee: DePuy Spine, Inc., Raynham, MA (US)

( * ) Notice: Subject to any disclaimer, the term of this patent is extended or adjusted under 35 U.S.C. 154(b) by 883 days.

(21) Appl. No.: 11/277,725

(22) Filed: Mar. 28, 2006

(65) Prior Publication Data

US 2007/0233261 A1    Oct. 4, 2007

(51) Int. Cl.
*A61F 2/44* (2006.01)
(52) U.S. Cl. .................................. 623/17.16; 606/279
(58) Field of Classification Search .... 623/17.11–17.16; 606/61, 69–71, 74, 77, 246–249, 257, 279
See application file for complete search history.

(56) References Cited

U.S. PATENT DOCUMENTS

| | | |
|---|---|---|
| 2,004,001 A | 6/1935 | Henkle |
| 3,867,728 A | 2/1975 | Stubstad et al. |
| 4,772,287 A | 9/1988 | Ray et al. |
| 4,904,260 A | 2/1990 | Ray et al. |
| 5,522,899 A | 6/1996 | Michelson |
| 5,562,738 A | 10/1996 | Boyd et al. |
| 5,676,702 A | 10/1997 | Ratron et al. |
| 5,702,450 A | 12/1997 | Bisserie et al. |
| 5,716,416 A | 2/1998 | Lin |
| 5,893,889 A | 4/1999 | Harrington |
| 5,928,284 A | 7/1999 | Mehdizadeh |
| 6,086,595 A | 7/2000 | Yonemura et al. |
| 6,156,040 A | 12/2000 | Yonemura et al. |
| 6,179,874 B1 | 1/2001 | Cauthen |
| 6,231,609 B1 | 5/2001 | Mehdizadeh |
| 6,440,168 B1 | 8/2002 | Cauthen |
| 6,468,311 B2 * | 10/2002 | Boyd et al. ................ 623/17.16 |
| 6,562,041 B1 | 5/2003 | Yonemura et al. |
| 6,572,653 B1 | 6/2003 | Simonson |
| 6,610,093 B1 | 8/2003 | Pisharodi |
| 6,645,248 B2 * | 11/2003 | Casutt ....................... 623/17.12 |

(Continued)

FOREIGN PATENT DOCUMENTS

EP    1198209    4/2002

(Continued)

*Primary Examiner* — Thomas C. Barrett
*Assistant Examiner* — Michael Araj
(74) *Attorney, Agent, or Firm* — Nutter McClennen & Fish LLP

(57) ABSTRACT

Methods and devices are provided for replacing a spinal disc. In an exemplary embodiment, artificial disc replacements and methods are provided wherein at least a portion of a disc replacement can be implanted using a posterolateral approach. With a posterolateral approach, the spine is accessed more from the side of the spinal canal through an incision formed in the patient's back. A pathway is created from the incision to the disc space between adjacent vertebrae. Portions of the posterolateral annulus, and posterior lip of the vertebral body may be removed to access the disc space, leaving the remaining annulus and the anterior and posterior longitudinal ligaments in tact. The disc implant can be at least partially introduced using a posterolateral approach, yet it has a size that is sufficient to restore height to the adjacent vertebrae, and that is sufficient to maximize contact with the endplates of the adjacent vertebrae.

22 Claims, 13 Drawing Sheets

U.S. PATENT DOCUMENTS

| | | |
|---|---|---|
| 6,679,915 B1 | 1/2004 | Cauthen |
| 6,692,495 B1 | 2/2004 | Zacouto et al. |
| 6,723,126 B1 | 4/2004 | Berry |
| 6,814,737 B2 | 11/2004 | Cauthen |
| 6,846,328 B2 | 1/2005 | Cauthen |
| 6,852,126 B2 | 2/2005 | Ahlgren |
| 6,881,228 B2 | 4/2005 | Zdeblick et al. |
| 6,893,465 B2 | 5/2005 | Huang et al. |
| 6,896,680 B2 | 5/2005 | Michelson |
| 6,896,701 B2 | 5/2005 | Boyd et al. |
| 7,052,515 B2 | 5/2006 | Simonson |
| 7,267,690 B2 * | 9/2007 | Felt ............................ 623/17.11 |
| 7,481,840 B2 | 1/2009 | Zucherman et al. |
| 7,591,853 B2 | 9/2009 | Felt et al. |
| 2001/0032017 A1 | 10/2001 | Alfaro et al. |
| 2003/0036798 A1 | 2/2003 | Alfaro et al. |
| 2003/0055427 A1 | 3/2003 | Graf |
| 2003/0135275 A1 | 7/2003 | Garcia et al. |
| 2003/0199982 A1 | 10/2003 | Bryan |
| 2003/0220643 A1 | 11/2003 | Ferree |
| 2004/0049280 A1 | 3/2004 | Cauthen |
| 2004/0073312 A1 | 4/2004 | Eisermann et al. |
| 2004/0138749 A1 | 7/2004 | Zucherman et al. |
| 2004/0138753 A1 | 7/2004 | Ferree |
| 2004/0143270 A1 | 7/2004 | Zucherman et al. |
| 2004/0143332 A1 | 7/2004 | Krueger et al. |
| 2004/0151618 A1 | 8/2004 | Bendiner et al. |
| 2004/0153157 A1 | 8/2004 | Keller |
| 2004/0153159 A1 | 8/2004 | Cauthen |
| 2004/0158254 A1 | 8/2004 | Eisermann |
| 2004/0158328 A1 | 8/2004 | Eisermann |
| 2004/0167538 A1 | 8/2004 | Gerber et al. |
| 2004/0181284 A1 | 9/2004 | Simonson |
| 2004/0181285 A1 | 9/2004 | Simonson |
| 2004/0186577 A1 | 9/2004 | Ferree |
| 2004/0225362 A1 | 11/2004 | Richelsoph |
| 2004/0225363 A1 | 11/2004 | Richelsoph |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0254644 A1 | 12/2004 | Taylor |
| 2004/0267369 A1 | 12/2004 | Lyons et al. |
| 2005/0033431 A1 | 2/2005 | Gordon et al. |
| 2005/0033432 A1 | 2/2005 | Gordon et al. |
| 2005/0033435 A1 | 2/2005 | Belliard et al. |
| 2005/0033437 A1 | 2/2005 | Bao et al. |
| 2005/0033439 A1 | 2/2005 | Gordon et al. |
| 2005/0043800 A1 | 2/2005 | Paul et al. |
| 2005/0043802 A1 | 2/2005 | Eisermann et al. |
| 2005/0049623 A1 | 3/2005 | Moore et al. |
| 2005/0065610 A1 | 3/2005 | Pisharodi |
| 2005/0085909 A1 | 4/2005 | Eisermann |
| 2005/0102027 A1 | 5/2005 | Ferree |
| 2005/0102029 A1 | 5/2005 | Blain |
| 2005/0102030 A1 | 5/2005 | Yuksel et al. |
| 2005/0107881 A1 * | 5/2005 | Alleyne et al. ............. 623/17.15 |
| 2005/0113918 A1 | 5/2005 | Messerli et al. |
| 2005/0113925 A1 | 5/2005 | Carli |
| 2005/0113926 A1 | 5/2005 | Zucherman et al. |
| 2005/0113928 A1 | 5/2005 | Cragg et al. |
| 2005/0113929 A1 | 5/2005 | Cragg et al. |
| 2005/0119747 A1 | 6/2005 | Fabris Monterumici et al. |
| 2005/0119752 A1 | 6/2005 | Williams et al. |
| 2005/0125061 A1 | 6/2005 | Zucherman et al. |
| 2005/0125062 A1 | 6/2005 | Biedermann et al. |
| 2005/0125063 A1 | 6/2005 | Matge et al. |
| 2005/0125065 A1 | 6/2005 | Zucherman et al. |
| 2005/0130929 A1 | 6/2005 | Boyd |
| 2005/0131536 A1 | 6/2005 | Eisermann et al. |
| 2005/0131540 A1 | 6/2005 | Trieu |
| 2005/0131541 A1 | 6/2005 | Trieu |
| 2005/0131542 A1 | 6/2005 | Benzel et al. |
| 2005/0131543 A1 | 6/2005 | Benzel et al. |
| 2005/0131544 A1 | 6/2005 | Kuras et al. |
| 2005/0171610 A1 | 8/2005 | Humphreys et al. |
| 2006/0293752 A1 * | 12/2006 | Moumene et al. ......... 623/17.13 |
| 2007/0299521 A1 | 12/2007 | Glenn et al. |

FOREIGN PATENT DOCUMENTS

| | | |
|---|---|---|
| EP | 1527759 | 5/2005 |
| EP | 1531765 | 5/2005 |
| EP | 1532948 | 5/2005 |
| EP | 1534193 | 6/2005 |
| EP | 1534194 | 6/2005 |
| EP | 1539051 | 6/2005 |
| EP | 1539052 | 6/2005 |
| WO | WO-9909896 | 3/1999 |
| WO | WO-03071992 | 9/2003 |
| WO | 2004002291 | 1/2004 |
| WO | WO-2004016205 | 2/2004 |
| WO | WO-2004016217 | 2/2004 |
| WO | 2004019828 | 3/2004 |
| WO | 2004019830 | 3/2004 |
| WO | 2004026186 | 4/2004 |
| WO | WO-2004098465 | 11/2004 |
| WO | WO-2004098466 | 11/2004 |
| WO | WO-2005011522 | 2/2005 |
| WO | WO-2005013862 | 2/2005 |
| WO | WO-2005037028 | 4/2005 |
| WO | WO-2005037148 | 4/2005 |
| WO | WO-2005039455 | 5/2005 |
| WO | WO-2005041793 | 5/2005 |
| WO | WO-2005041818 | 5/2005 |
| WO | WO-2005046534 | 5/2005 |
| WO | WO-2005051228 | 6/2005 |
| WO | WO-2005051243 | 6/2005 |
| WO | WO-2005051246 | 6/2005 |
| WO | WO-2005053579 | 6/2005 |
| WO | WO-2005053580 | 6/2005 |

* cited by examiner w

ARTIFICIAL DISC REPLACEMENT USING POSTERIOR APPROACH

FIELD OF THE INVENTION

The present invention relates to intervertebral disc replacement devices, and methods for implanting intervertebral disc replacement devices.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the affected disc and subsequent fusion of the opposing vertebra to one another. Spinal fusion consists of fusing the adjacent vertebrae through the disc space (the space previously occupied by the spinal disc interposed between the adjacent vertebral bodies). Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process.

More recently, artificial disc replacements have been developed that allow one or more degrees of freedom between the adjacent vertebrae, thereby restoring function to the vertebrae. Surgical procedures for replacing intervertebral disc material, rather than fusing of the vertebrae, have included both anterior approaches and posterior approaches to the spinal column. The anterior approach to the spinal column is complicated by the internal organs that must be bypassed or circumvented to access the vertebrae. The posterior approach (from the back of the patient) encounters the spinous process, superior articular process, and the inferior articular process. These features may be removed to ease insertion of the artificial disc replacement into the intervertebral space, as the disc replacement must have a height sufficient to restore normal height to the adjacent vertebrae, and it must have a depth and width, or surface area, that is sufficient to ensure contact with the peripheral bone, e.g., cortical bone, surrounding the vertebral endplates.

Accordingly, there remains a need for improved methods and devices for replacing a disc.

SUMMARY OF THE INVENTION

The present invention provides various methods and devices for replacing a disc. In one embodiment, an artificial disc replacement implant is provided and includes a central component having a superior member adapted to be positioned adjacent to an endplate of a superior vertebra, and an inferior member adapted to be positioned adjacent to an endplate of an adjacent inferior vertebra. The superior and inferior members can be movable relative to one another. The central component can also include leading and trailing ends and opposed first and second lateral sides extending between the leading and trailing ends. At least one of the lateral sides can include a mating element formed thereon. The implant can also include at least one lateral component having a mating element removably matable to the mating element on at least one of the first and second lateral sides of the central component. The central component and the lateral component(s) can also have a superior and inferior footprint, when mated, that is substantially equal to a superior and inferior footprint of superior and inferior vertebrae between which the implant is adapted to be positioned.

While the central component can have a variety of configurations, in one embodiment the superior and inferior members each include a bone-contacting surface adapted to be positioned adjacent to bone, and an opposed articulating surface. The articulating surfaces can be configured to move relative to one another to allow movement between the superior and inferior members. For example, the articulating surface on one of the superior and inferior members can include a concave cavity formed therein, and the articulating surface on the other one of the superior and inferior members can include a convex protrusion formed thereon and adapted to be received within the concave cavity.

The lateral component(s) can also have a variety of configurations. For example, the lateral component(s) can be substantially U-shaped such that the lateral component(s) is elastic. In another embodiment, the lateral component(s) can include a superior lateral member removably matable to the superior member of the central component, and inferior lateral member removably matable to the inferior member of the central component. The superior and inferior lateral members can be mated to one another by a compressible or elastic element, such as an elastomer, extending therebetween. In another embodiment, the lateral component(s) can include a first lateral component having a superior lateral member and an inferior lateral member, and a second lateral component having a superior lateral member and an inferior lateral member. The first lateral component can be removably matable to the first lateral side of the central component, and the second lateral component can be removably matable to the second lateral side of the central component.

The implant can also include other features, such as one or more surface protrusions formed on at least one of the superior and inferior members. In one embodiment, the superior and inferior members can each include a keel extending between the leading and trailing ends. In an exemplary embodiment, the keel has a height that increase in from the leading end to the trailing end, and the keel extends substantially parallel to the opposed lateral sides. In other embodiment, the implant can include one or more markers, such as a cut-out, radiolucent or radiopaque marker, or other feature formed on the superior and/or inferior members to facilitate positioning of the members.

In another embodiment, an artificial disc replacement implant is provided for insertion within a disc space formed between adjacent vertebral bodies. The implant can include a central component including superior and inferior members movable relative to one another, and having a superior surface adapted to be positioned adjacent to a superior endplate of a superior vertebra, and an inferior surface adapted to be positioned adjacent to an inferior endplate of an inferior vertebra. The central component can also include opposed leading and trailing ends and opposed lateral sides extending between the leading and trailing ends. A maximum width extending between the opposed lateral sides can be less than a width of a posterolateral surgical access window extending into a disc space into which said central component is adapted to be inserted, and a length extending between the leading and trailing ends can be sufficient to allow the leading and trailing ends to contact peripheral bone that surrounds the superior and inferior endplates which the central component is adapted to be positioned between. The central component can also include a surface area on each of the superior and inferior surfaces that is smaller than a surface area of the superior and inferior endplates which the central component is adapted to be positioned between. In certain exemplary embodiments, the central component can be in the shape of a parallelogram. The implant can also include at least one lateral component removably matable to a lateral side of the central component. For example, the implant can include a superior lateral member adapted to mate to the superior member of the central component, and an inferior lateral member adapted to mate to the inferior member of the central component.

A method for implanting a disc replacement is also provided and can include inserting a central component along an axis extending in a posterior-lateral direction into a disc space formed between adjacent vertebrae, and inserting at least one lateral component along an axis extending in a posterior-anterior or a posterolateral direction into the disc space to couple the lateral component to the central component. Prior to inserting the central component, a surgical access window that extends from an incision formed in a patient's skin at a location posterior-lateral to the patient's spinal column to a disc space is preferably formed between adjacent superior and inferior vertebrae, and a disc disposed within the disc space is removed. The access window can be formed by removing a facet joint extending between the adjacent superior and inferior vertebrae. The adjacent superior and inferior vertebrae can also be distracted from a contra-lateral or ipsi-lateral side prior to inserting the central component. Various techniques can also be used to insert the lateral component(s), and in one embodiment a first lateral component can be inserted along a first axis extending in a generally posterior-anterior direction into the disc space to couple the first lateral component to a first lateral side of the central component, and a second first lateral component can be inserted along a second axis extending in a generally posterior-anterior direction into the disc space to couple the second lateral component to a second, opposed lateral side of the central component. In other embodiments, the central component can include at least one protrusion, such as a keel, formed on at least one of a superior and inferior surface thereof, and the keel can be aligned with the axis of the surgical access window. A marker, such as a cut-out, can be formed in the keel, and the method can include imaging the cut-out to determine a position of the central component relative to the adjacent superior and inferior vertebrae.

In another embodiment, a method for implanting an artificial disc replacement is provided and includes inserting a central component along a posterolateral axis of a surgical access window extending posterolaterally into a disc space between adjacent superior and inferior vertebrae. The central component can have a width that is less than a width of the surgical access window, and a superior member that is positioned adjacent to a superior endplate of the superior vertebra and an inferior member that is positioned adjacent to an inferior endplate of the inferior vertebra. The superior and inferior members can maintain the adjacent superior and inferior vertebrae at a distance apart from one another, and they can be movable relative to one another to allow movement between the adjacent superior and inferior vertebrae. In an exemplary embodiment, the central component includes a leading end and a trailing end, and the leading and trailing ends of the central component are positioned in contact with peripheral bone surrounding the superior and inferior endplates. The method can further include rotating one of the superior and inferior members relative to the other one of the superior and inferior members to position the rotated member along a contra-lateral axis.

In another embodiment, a method for implanting an artificial disc replacement is provided and includes inserting a superior member along a first posterolateral axis of a first surgical access window extending posterolaterally into a disc space between adjacent superior and inferior vertebrae. The superior member can have a width that is equal to or less than a width of the first surgical access window. The method further includes inserting an inferior member along a second posterolateral axis of a second surgical access window extending posterolaterally into a disc space between adjacent superior and inferior vertebrae. The second posterolateral axis can be located on the contralateral side of the vertebra from the first posterolateral axis, and the inferior member can have a width that is equal to or less than a width of the second surgical access window. The superior member is positioned adjacent an endplate of the superior vertebrae, and the inferior member is positioned adjacent an endplate of the inferior vertebra such that the superior and inferior members maintain the adjacent superior and inferior vertebrae at a distance apart from one another.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for replacing a spinal disc. In an exemplary embodiment, artificial disc replacements and methods are provided wherein at least a portion of a disc replacement can be implanted using a posterolateral approach. The posterolateral annulus, and posterior lip of the vertebral bodies may be removed to access the disc space, leaving the remaining annulus and the anterior and posterior longitudinal ligaments in tact. A portion or all of the facet joints may be removed to provide better access to the disc space. The posterolateral pathway is referred to herein as a posterolateral surgical access window. A typical posterolateral access window has a maximum width of about 13 mm without displacing nerves or dural elements and a maximum height of about 11 mm without distraction. The present invention provides disc implants which can be at least partially introduced using a posterolateral approach, yet that have a size that is sufficient to restore height to the adjacent vertebrae, and that is sufficient to maximize contact with the endplates of the adjacent vertebrae.

Figure 1A:
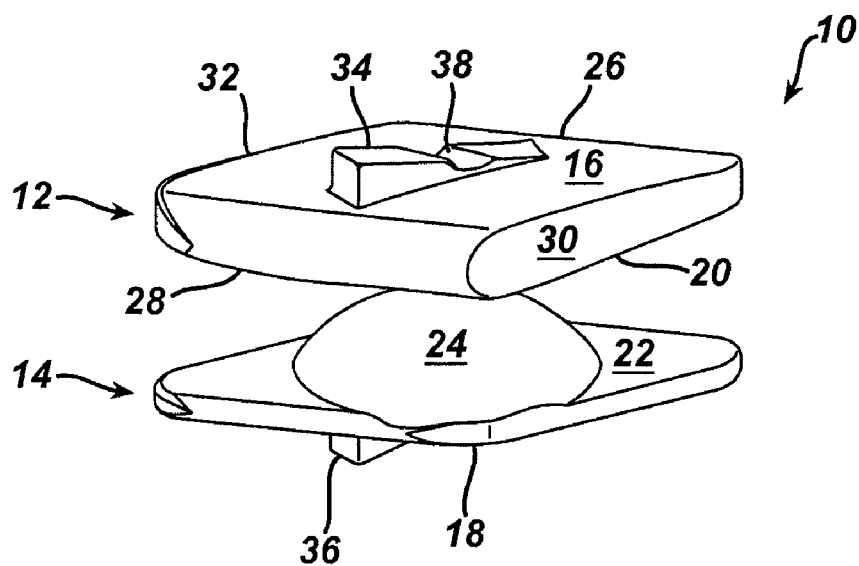
FIG. 1A is a side perspective view of one exemplary embodiment of an implant that can be introduced between adjacent vertebrae using a posterolateral approach.
Figure 1B:
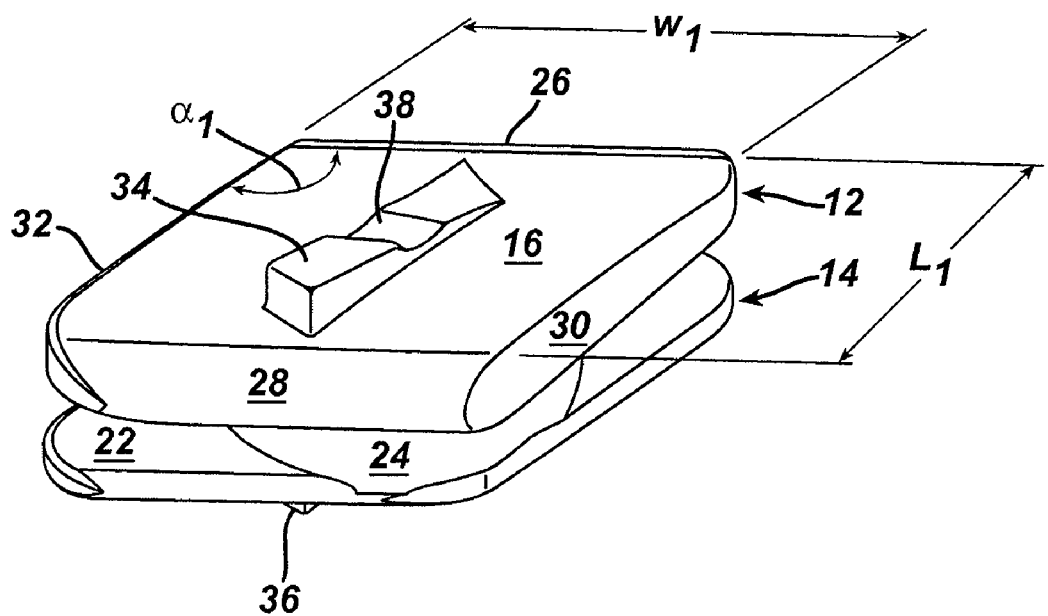
FIG. 1B is a top perspective view of the implant shown in FIG. 1A.

FIGS. 1A and 1B illustrate one exemplary embodiment of an implant that can be introduced through a posterolateral surgical access window. As shown, the implant 10 generally includes a superior member 12 adapted to be positioned adjacent to an endplate of a superior vertebra, and an inferior member 14 adapted to be positioned adjacent to an endplate of an inferior vertebra. In particular, each member 12, 14 includes a bone-contacting surface 16, 18 configured to be positioned adjacent to an endplate of a vertebra, and an opposed mating or articulating surface 20, 22 configured to be positioned adjacent to one another. Together, the superior and inferior members 12, 14 are configured to restore height to the adjacent vertebrae, and they can optionally move relative to one another to restore motion to the adjacent vertebrae. While various techniques can be used to allow the superior and inferior members 12, 14 to move relative to one another, in one exemplary embodiment the mating surfaces 20, 22 on the superior and inferior members 12, 14 are articulating surfaces. For example, at least one of the members, e.g., the superior member 12, can include a concave recess formed therein, and the other member, e.g., the inferior member 14, can include a convex or spherical member 24 formed thereon. The spherical member 24 can be movably disposed within the concave recess to allow movement between the superior and inferior members 12, 14, thereby allowing movement between the vertebrae.

Figure 1C:
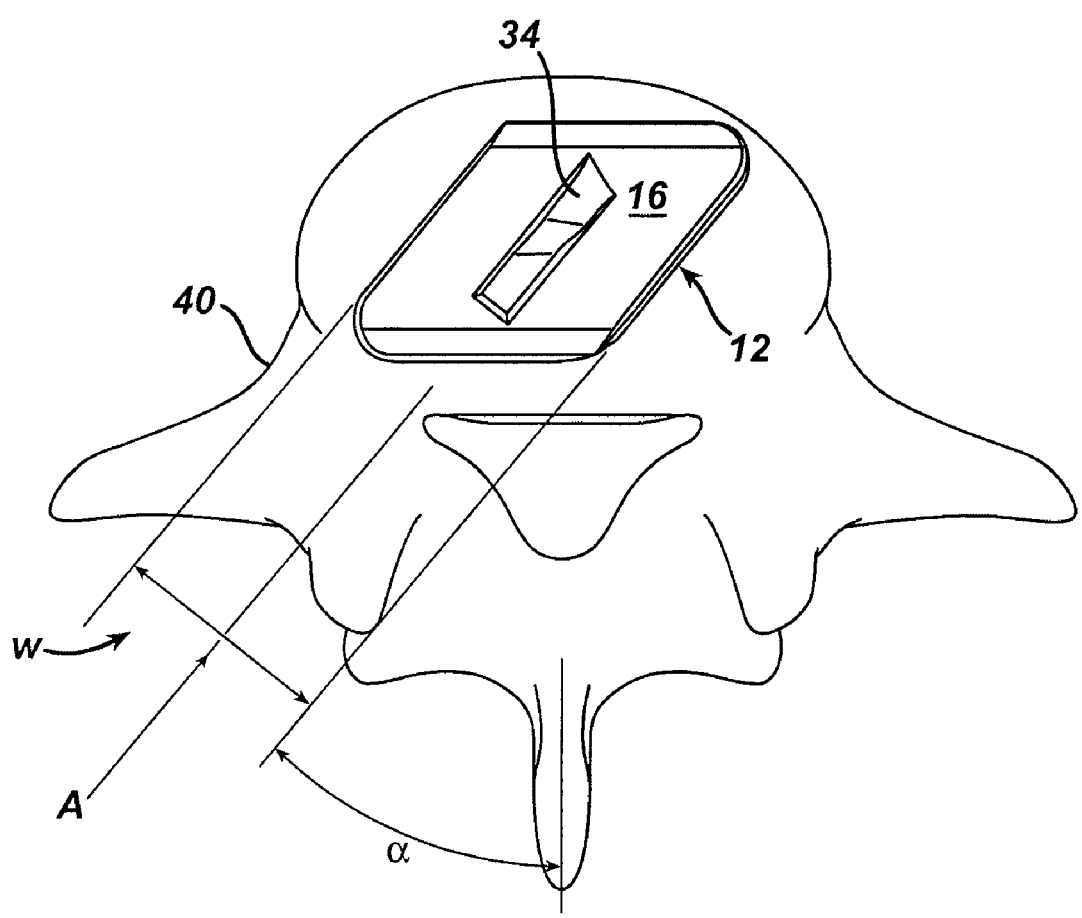
FIG. 1C is a top view of the implant shown in FIGS. 1A-1B positioned on a vertebral body, showing a posterolateral surgical access window for introducing the implant.

As explained above, the implant 10 can have a configuration that allows the implant 10 to be introduced through a posterolateral approach surgical access window, yet that restores height to the adjacent vertebrae and maximizes contact with the endplates. As shown in FIGS. 1A and 1B, the implant 10 includes opposed leading and trailing ends 26, 28 and opposed lateral sides 30, 32 extending between the leading and trailing ends 26, 28. The width $w_1$ extending between the opposed lateral sides 30, 32 can be equal to or less than a width of a posterolateral access window into which the implant 10 is adapted to be inserted, and in an exemplary embodiment the width $w_1$ is less than about 20 mm. The length $L_1$ of the implant 10 extending between the leading and trailing ends 26, 28 can also vary, but in certain exemplary embodiments the length $L_1$ is sufficient to allow the leading and trailing ends 26, 28 of the implant 10 to contact peripheral bone, e.g., cortical bone, surrounding the superior and inferior endplate, and in particular to contact the cortical bone or both the posterior and anterior sides of the disc space. By way of non-limiting example, the length $L_1$ can be in the range of about 25 mm to 30 mm. As a result of the length $L_1$ and width $w_1$ of the implant 10, the surface area on each of the superior and inferior surfaces of the implant 10 is smaller than a surface area of the superior and inferior endplates which the implant 10 is adapted to be positioned between. The particular shape of the implant, however, is preferably maximized to maximize the surface area and to occupy the space defined by a posterolateral axis window. As shown in FIG. 1C, the access window extends in a posterolateral direction at an angle of about 40° from the axis of the spinous process, and the access window has a width of about 20 mm. The illustrated implant 10 has a shape in the form of a parallelogram with the opposed lateral sides 30, 32 extending at an angle $\alpha_1$ that is greater than 90° relative to the leading and trailing edges 26, 28. This will allow the implant 10 to be introduced through and along an axis A of a posterolateral access window W, as shown in FIG. 1C, and to be positioned diagonally across the endplates of the adjacent vertebrae. The shape of the implant 10 will also allow the implant to occupy the entire space defined by the access window, thereby maximizing the size of the implant and thus the surface contact between the implant and the endplates of the adjacent vertebrae.

The implant 10 can also include other features to facilitate use of the device. For example, as shown in FIGS. 1A-1C the superior and/or inferior members 12, 14 can include a protrusion, such as a keel 34, 36, formed on the bone-contacting surfaces 16, 18 thereon to facilitate insertion of the device. Each keel 34, 36 preferably extends in a posterolateral direction, substantially parallel to the lateral sides of the implant 10, such that it can be used to guide the implant 10 along the axis A of the access window W. The implant 10 can also include one or more features, such as a marker, to confirm the proper position of the implant 10 once it is implanted. For example, as shown in FIGS. 1A-1C, the keel 34 includes a cut-out 38 formed therein. The cut-out 38 can be viewed on an image, such as an X-ray image, to ensure that the implant 10 is properly positioned within the disc space. In other embodiments, the marker can be a radiopaque or radiolucent marker formed on the implant. A person skilled in the art will appreciate that a variety of other techniques can be used to facilitate insertion and/or alignment of the implant 10, and that the implant can include a variety of other features.

Figure 2A:
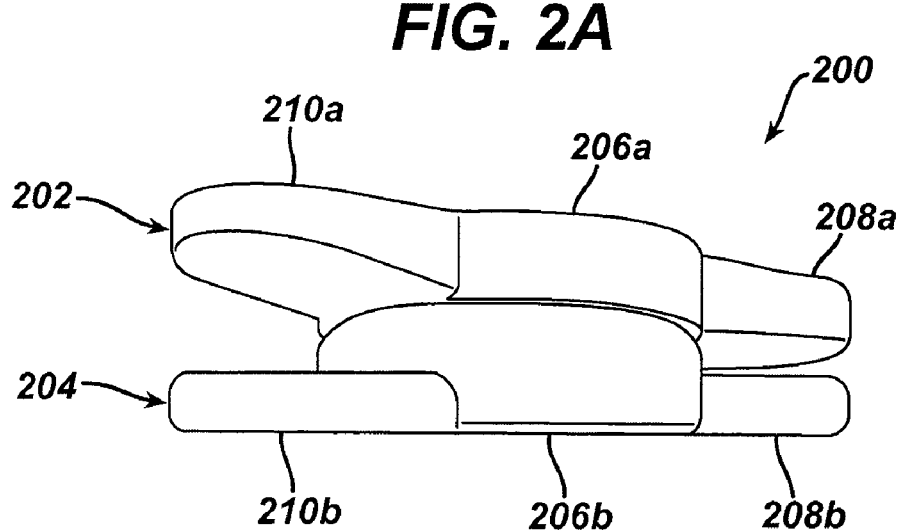
FIG. 2A is a side perspective view of another embodiment of an implant that can be introduced between adjacent vertebrae using a posterolateral approach.
Figure 2B:
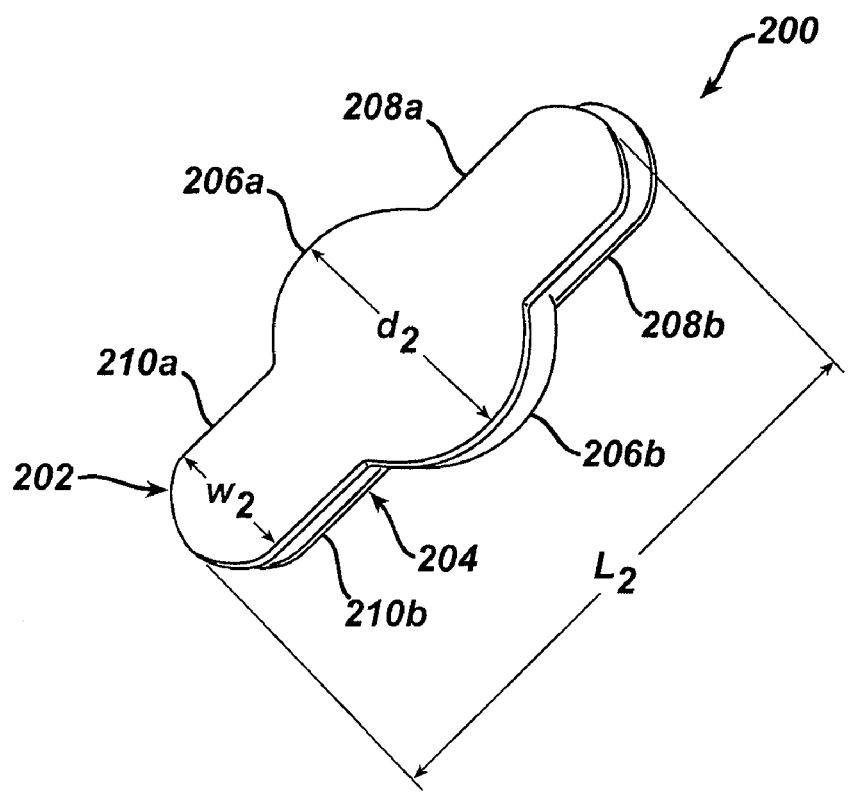
FIG. 2B is a top perspective view of the implant shown in FIG. 2A.
Figure 2C:
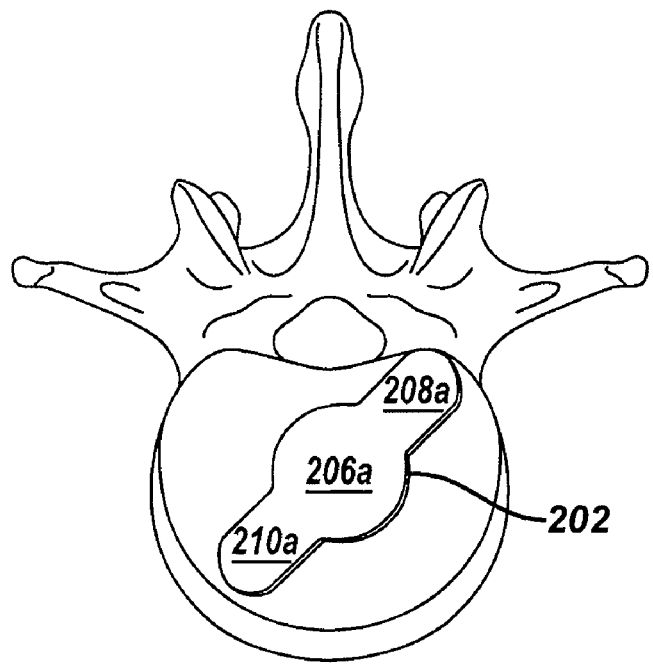
FIG. 2C is a top view of the implant shown in FIGS. 2A-2B positioned on a vertebral body.

As indicated above, the implant can have a variety of other shapes and sizes to allow the implant to be introduced through a posterolateral access window. FIGS. 2A-2C illustrate another embodiment of an implant 200 which generally includes superior and inferior members 202, 204 similar to those described with respect to FIGS. 1A-1B. In particular, the superior and inferior members 202, 204 are adapted to be positioned between adjacent vertebrae, and they are movable relative to one another to allow movement of the adjacent vertebrae. In this embodiment, however, each member 202, 204 of the implant 200 has an elongate shape with a central portion 206a, 206b having opposed leading and trailing extensions 208a, 208b, 210a, 210b. Each central portion 206a, 206b can have a circular shape with a diameter $d_2$ that is greater than a width $w_2$ of the opposed leading and trailing extensions 208a, 208b, 210a, 210b, but that is less than or equal to a width of a posterolateral access window. The circular shape of the central portion 206a, 206b can allow the central portions 206a, 206b to articulate relative to one another. For example, concave and convex surfaces can be formed on the articulating surface of each member 202, 204 to allow movement therebetween. The implant can also have a length $L_2$ that varies, but in an exemplary embodiment the length $L_2$ is preferably sufficient to allow the leading and trailing extensions 208a, 208b, 210a, 210b to contact cortical bone surrounding the superior and inferior endplates.

Figure 2D:
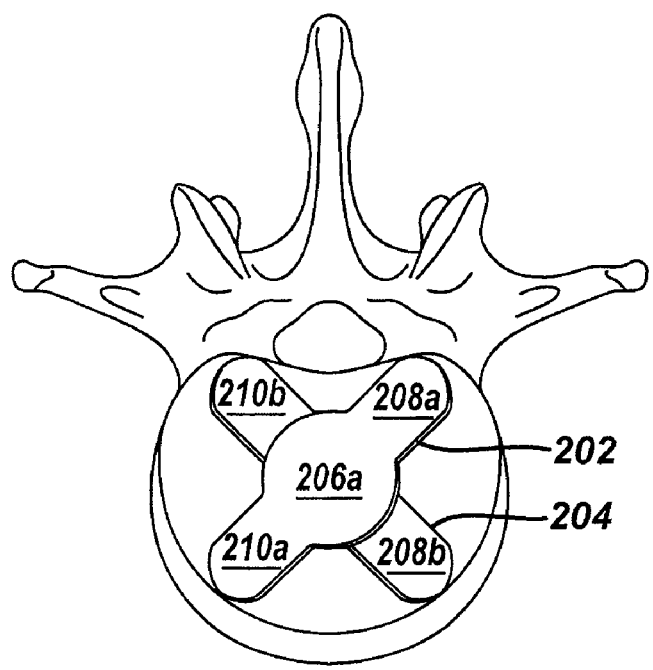
FIG. 2D is a top view of the implant shown in FIG. 2C having one of the superior and inferior members of the implant rotated about 90°.

In use, as shown in FIG. 2C, the diameter $d_2$ of the central portions 206a, 206b and the width $w_2$ of the extensions 208a, 208b, 210a, 210b of the implant 200 allow the implant 200 to be introduced through the posterolateral surgical access window, i.e., diagonally into the disc space. The length $L_2$ allows the leading and trailing extensions 208a, 208b, 210a, 210b of the implant 200 to contact the cortical bone adjacent to the posterior and anterior sides of the vertebrae, as shown. In order to further increase stability of the implant, one of the superior and inferior members 202, 204 can be rotated relative to the other member. FIG. 2D illustrates the members 202, 204 rotated 90° relative to one another. This configuration allows the implant 200 to contact cortical bone at four locations, two on each of the posterior and anterior sides of the disc space, resulting in increased stability of the implant 200. A person skilled in the art will appreciate that members 202, 204 can be rotated at any angle relative to one another to increase contact with the endplates of adjacent bone, or the superior and inferior members 202, 204 can remain in alignment with one another. In other embodiments, the members 202, 204 can be introduced through separate windows formed on a contralateral sides of the vertebra to position the members as shown in FIG. 2D.

In other embodiments, an artificial disc implant can include a central component and one or more lateral components that mate to the central component. The central component can be similar to the implants previously described above, or it can have various other configurations, but it is preferably configured to be introduced through a posterolateral surgical access window. The lateral component(s) are configured to mate to the lateral side(s) of the central component to maximize contact between the implant and the endplates of the adjacent vertebrae. In an exemplary embodiment, the lateral components are configured to be introduced using a posterior approach, however virtually any technique known in the art can be used for implanting and mating the lateral component (s) to the central component.

Figure 3A:
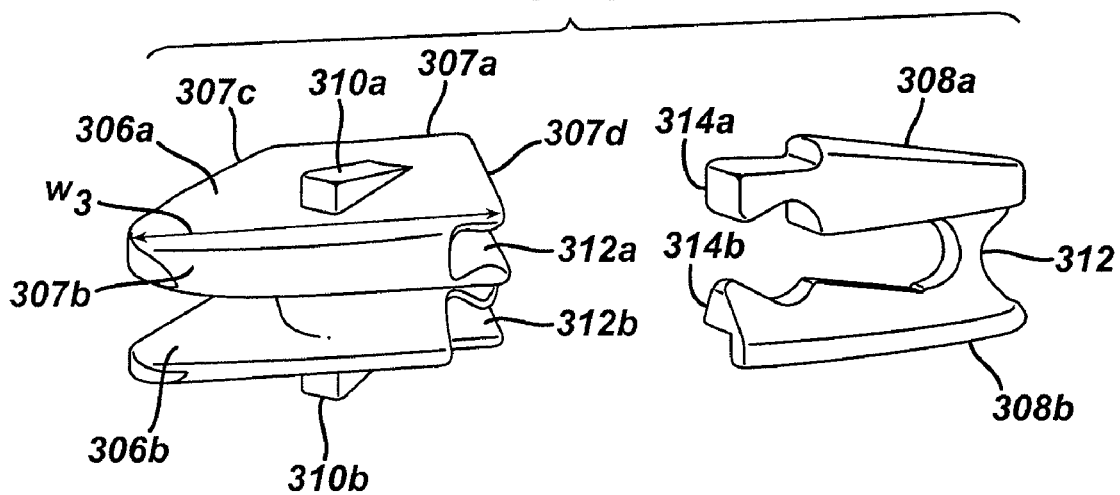
FIG. 3A is an exploded perspective view of another exemplary embodiment of an implant having a central component that can be introduced between adjacent vertebrae using a posterolateral approach and a lateral component that can mate to the central component.
Figure 3B:
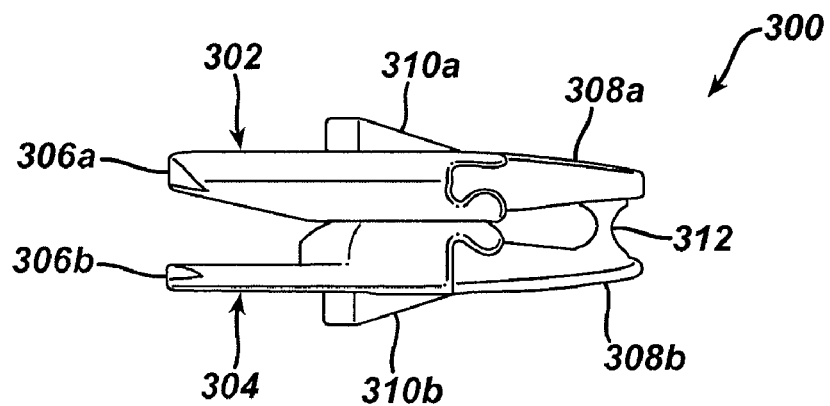
FIG. 3B is a side view of the implant shown in FIG. 3A in an assembled configuration.
Figure 3C:
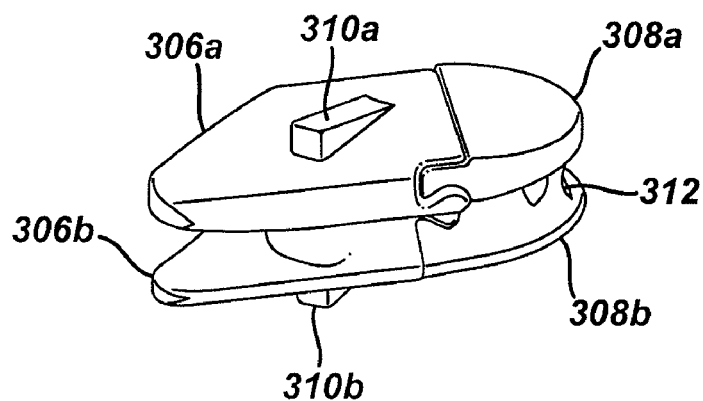
FIG. 3C is a top perspective view of the implant shown in FIG. 3A in an assembled configuration.

FIGS. 3A-3C illustrate one exemplary embodiment of an implant having a central component and a lateral component that mates to a lateral side of the central component. The configuration of the central component can vary, and it can include a single member or superior and inferior members 306a, 306b, as shown. The superior and inferior members 306a, 306b can be similar to members 12 and 14 previously described with respect to FIGS. 1A-1B, and in particular the members 306a, 306b can include opposed leading and trailing ends 307a, 307b and opposed lateral sides 307c, 307d extending therebetween. The members 306a, 306b can also be configured to move relative to one another to allow movement of the adjacent vertebrae. This can be achieved using, for example, concave and convex articulating surfaces. The superior and inferior central members 306a, 306b also preferably have a shape and size that allows the members to be introduced through a posterolateral access window. In the illustrated embodiment, each central member 306a, 306b has a shape in the form of a trapezoid, with non-parallel opposed lateral sides. A first lateral side 307c extends between the leading and trailing ends 307a, 307b at an angle that is less than or greater than 90° relative to the leading and trailing ends 307a, 307b. A second lateral side 307d extends perpendicularly between the leading and trailing ends 307a, 307b. The size can also vary, however in an exemplary embodiment the maximum width $w_3$ extending between the opposed lateral sides 307c, 307d can be equal to or less than a width of a posterolateral access window into which the central members 306a, 306b are adapted to be inserted, and the length $L_3$ extending between the leading and trailing ends 307a, 307b can be sufficient to allow the leading and trailing ends 307a, 307b of each central member 306a, 306b to contact cortical bone surrounding the disc space into which the implant 300 is inserted. As further shown, one of the lateral sides, e.g., the second lateral side 307d, of each of the superior and inferior central members 306a, 306b can include a mating element configured to mate with the lateral component. While the mating element can vary, in the illustrated embodiment a slot or groove 312a, 312b is formed in and extends along at least a portion of the straight lateral side 307a of each of the superior and inferior central members 306a, 306b. The grooves 312a, 312b are configured to receive complementary protrusions or tongues formed on the lateral component, as will be discussed below.

The lateral component can also include superior and inferior members 308a, 308b. The members 308a, 308b can vary in size and shape, but they are preferably configured to increase contact between the implant 300 and the endplates of the adjacent vertebrae. In the illustrated embodiment, each lateral member 308a, 308b has a semi-circular shape with a substantially straight edge and a curved portion extending between the ends of the straight edge. The straight edge of each lateral member 308a, 308b includes a mating element that is adapted to allow each lateral member 308a, 308b to mate to a mating component disposed on or formed within the second lateral side of each central member 306a, 306b. As shown in FIGS. 3A-3C, each lateral member 308a, 308b includes a tongue 314a, 314b extending substantially along the length of the straight edge thereof. The tongues 314a, 314b can be slidably disposed within the grooves 312a, 312b formed in the central members 306a, 306b to mate the superior and inferior lateral members 308a, 308b to the central members 306a, 306b. When mated, the central members 306a, 306b and the lateral members 308a, 308b can from an implant that has a surface area that is greater than at least 50% of a surface area of a vertebral endplate to maximum contact with the endplates, and more preferably that is greater than about 75% of a surface area of a vertebral endplate.

A person skilled in the art will appreciate that a variety of other mating techniques can be used to mate the central members 306a, 306b and the lateral members 308a, 308b of the implant 300, such as a dovetail connection, a pin-and-bore arrangement, etc. The mating connection can also include a stop that is adapted to prevent the lateral members 308a, 308b from sliding past the leading end of the central members 306a, 306b. When mated, this positions the leading and trailing edges of the lateral members 308a, 308b substantially flush with the leading and trailing edges of the central members 306a, 306b, as shown in FIGS. 3B-3C. While various techniques can be used to form a stop, in one embodiment a terminal end surface (not shown) can be formed within each groove 312a, 312b adjacent to the leading end of each central member 306a, 306b. As a result, the tongue 314a, 314b on each of the superior and inferior lateral members 308a, 308b will abut the end surface.

The implant 300 can include other features to facilitate use of the device, such as bone-engaging surface features, one or more keels 310a, 310b formed on the bone-contacting surfaces of the implant 300, or other elements to facilitate use and positioning of the implant. FIGS. 3A-3C illustrates keels similar to those previously described above in relation to FIGS. 1A-1C. FIGS. 3A-3C also illustrate a strut 312 extending between the superior and inferior lateral members 308a, 308b, which will be discussed in more detail below.

Figure 3D:
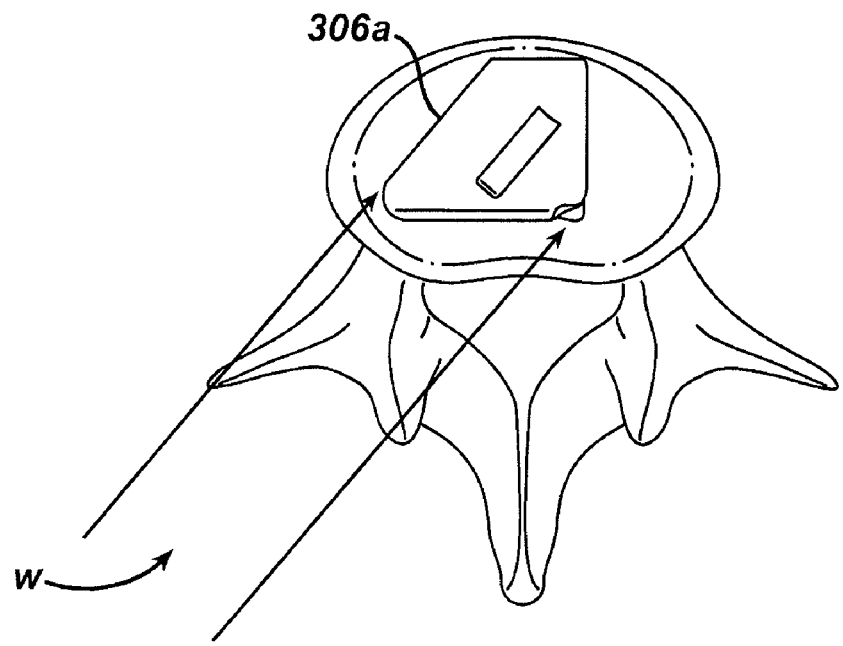
FIG. 3D is a top view of a central portion of the implant of FIGS. 3A-3C positioned on a vertebral body, showing a posterolateral surgical access window for introducing the central portion.
Figure 3E:
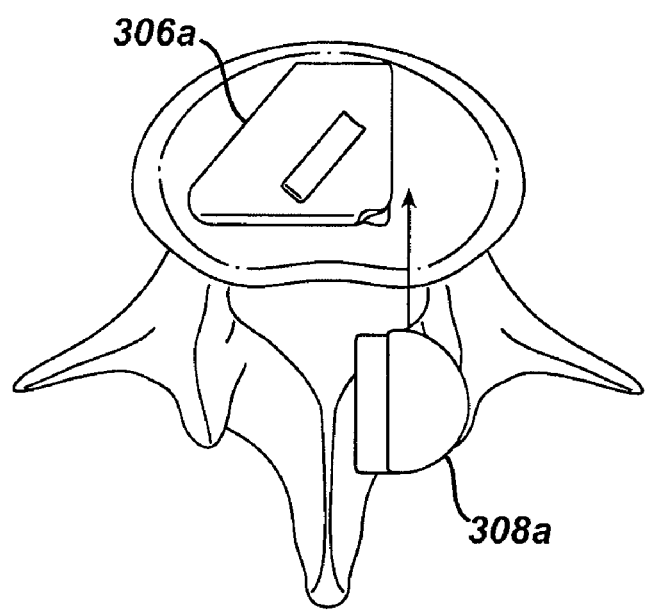
FIG. 3E is a top view of the central portion of the implant of FIG. 3D positioned on a vertebral body, showing a lateral component about to be introduced using a posterior approach to mate to the central component.

In use, as shown in FIGS. 3D and 3E, the central members 306a, 306b of the implant 300 can be introduced through the posterolateral surgical access window w to position the implant within the disc space. As shown, the shape and size of the central component occupies the space defined by the posterolateral access window, except for a region near the lateral side 307d of the implant which mates to the lateral component. The implant also has a length that allows the leading and trailing ends of the central members 306a, 306b to contact the cortical bone adjacent to the posterior and anterior sides of the vertebrae. In order to further maximize contact with the endplates of the adjacent vertebrae, the lateral members 308a, 308b can be introduced using, for example, a posterior approach, as shown in FIG. 3E. As the lateral members 308a, 308b are introduced into the disc space, the lateral members 308a, 308b can be mated to the central members 306a, 306b by sliding the complementary tongues 314a, 314b into the grooves 312a, 312b of the central members 306a, 306b.

Figure 4A:
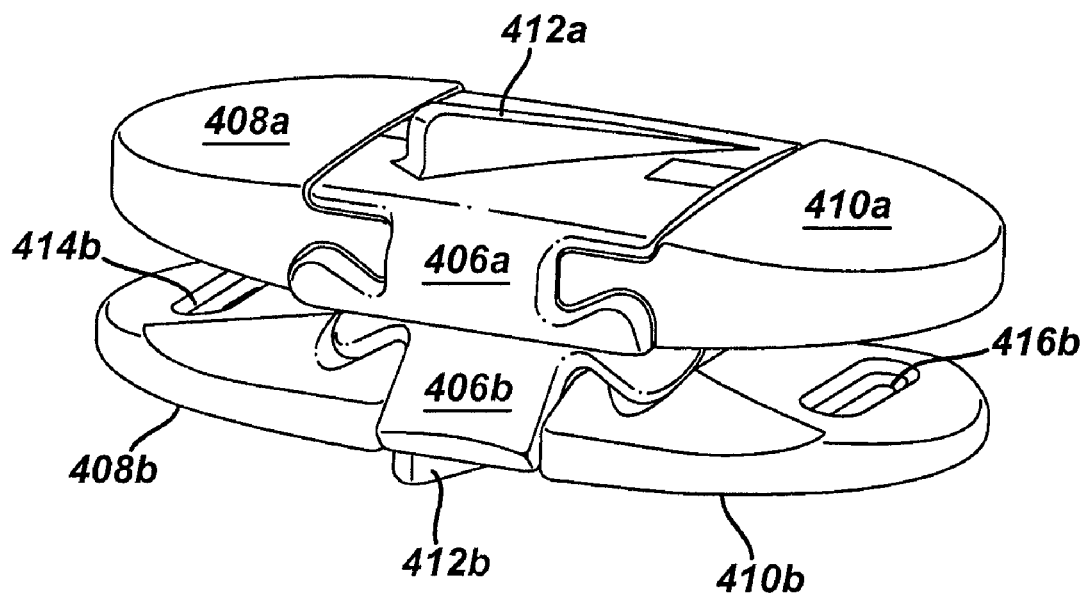
FIG. 4A is a perspective view of another exemplary embodiment of an implant having a central component that can introduced between adjacent vertebrae using a posterolateral approach and opposed lateral components that can mate to the central component.
Figure 4B:
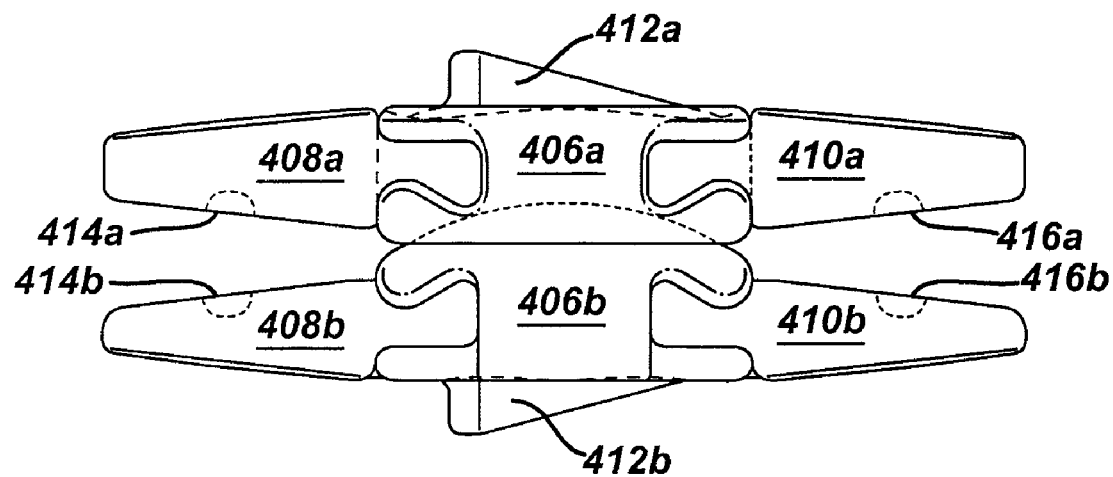
FIG. 4B is a side view of the implant shown in FIG. 4A.

FIGS. 4A-4B illustrate another embodiment of an implant having a central component and first and second lateral components. In this embodiment, the implant 400 includes left and right lateral components that mate to the central component. In particular, the central component includes superior and inferior members 406a, 406b, the left lateral component includes superior and inferior lateral members 408a, 408b, and the right lateral component includes superior and inferior lateral members 410a, 410b.

Figure 4C:
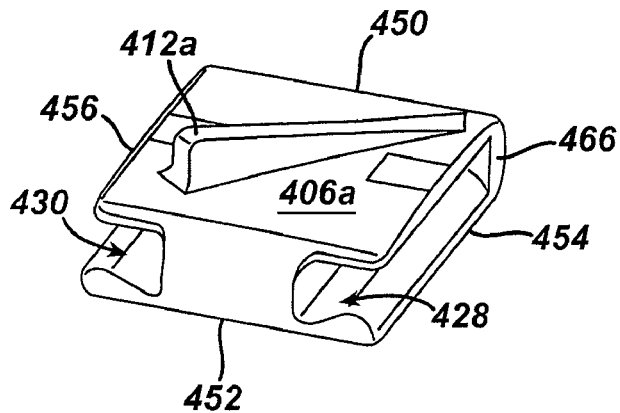
FIG. 4C is a perspective view of a superior central component of the implant shown in FIGS. 4A-4B.
Figure 4D:
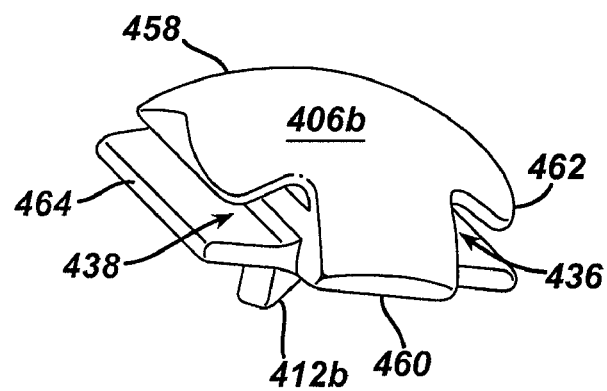
FIG. 4D is a perspective view of an inferior central component of the implant shown in FIGS. 4A-4B.

The superior and inferior central members 406a, 406b, which are shown in more detail in FIGS. 4C and 4D, respectively, are similar to the superior and inferior central members 12, 14 previously described with respect to FIGS. 1A and 1B. The members 406a, 406b, however, each have a generally square or rectangular shape with opposed leading and trailing ends 450, 452, 458, 460 and opposed lateral sides 454, 456, 462, 464 extending therebetween. Each central member 406a, 406b can include an articular surface to allow the superior and inferior central members 406a, 406b to move relative to one another. FIG. 4C illustrates a concave recess formed in the superior central member 406a, and FIG. 4D illustrates a convex surface formed on the inferior central member 406b. The convex surface can be movably disposed within the concave recess to allow movement between the superior and inferior central members 406a, 406b, and thereby allow movement between adjacent superior and inferior vertebrae between which the implant 400 is disposed. As with the embodiment shown in FIGS. 1A-1B, the central members 406a, 406b can also have a size that allows the central members to be introduced through a posterolateral access window. The size can also be configured to allow the leading the trailing ends 450, 452, 458, 460 of the central members 406a, 406b to contact cortical bone surrounding the disc space in which the implant 400 is inserted. The central members 406a, 406b can also include other features to facilitate use of the implant 400, such as one or more keels 412a, 412b formed on the bone-contacting surfaces of the central members 406a, 406b to facilitate insertion of the implant 400, similar to those described above in relation to FIGS. 1A-1C.

Figure 4E:
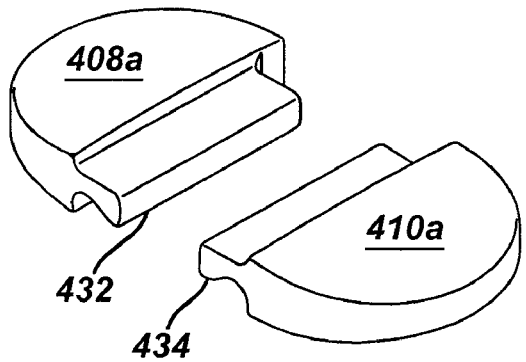
FIG. 4E is a perspective view of first and second superior lateral components of the implant shown in FIGS. 4A-4B.
Figure 4F:
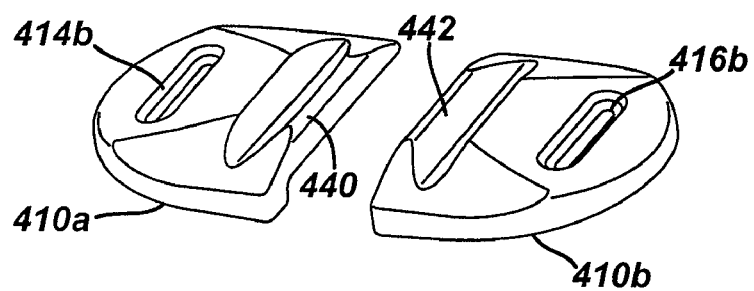
FIG. 4F is a perspective view of first and second inferior lateral components of the implant shown in FIGS. 4A-4B.

The superior left and right lateral members 408a, 408b are shown in more detail in FIG. 4E, and the inferior left and right lateral members 410a, 410b are shown in more detail in FIG. 4F. As shown, each lateral member 408a, 408b, 410a, 410b has a semi-circular shape with a substantially straight edge and a curved portion extending between the ends of the straight edge. Such a shape allows the lateral members to mate to the central component to thereby form a disc implant that substantially occupies a disc space, i.e., that has a footprint that matches a footprint of an endplate of a vertebra, as will be discussed in more detail below. As further shown, the straight edge of each lateral member 408a, 408b, 410a, 410b includes a mating element that is adapted to allow each lateral member 408a, 408b, 410a, 410b to mate to the corresponding mating elements formed on or within the opposed lateral sides of the central members 406a, 406b. While various mating techniques can be used, FIGS. 4A-4F illustrate a tongue-and-groove connection similar to that previously described with respect to FIGS. 3A-3B. In particular, the superior central member 406a includes grooves 428, 430 formed within opposed lateral sides 454, 456 thereof, and the inferior central member 406b includes grooves 436, 438 formed within opposed lateral sides 462, 464 thereof. Each groove 428, 430, 436, 438 is sized to receive a complementary tongue 432, 434, 440, 442 formed on a lateral member 408a, 408b, 410a, 410b. Each tongue 432, 434, 440, 442 extends along the length of the lateral members 408a, 408b, 410a, 410b. The mating elements can also include a stop that is adapted to prevent the lateral members 408a, 408b, 410a, 410b from sliding past the leading end of the central members 406a, 406b. FIG. 4C illustrates a stop 466 that forms a terminal end surface of the groove 428 in the superior central member 406a.

Figure 4G:
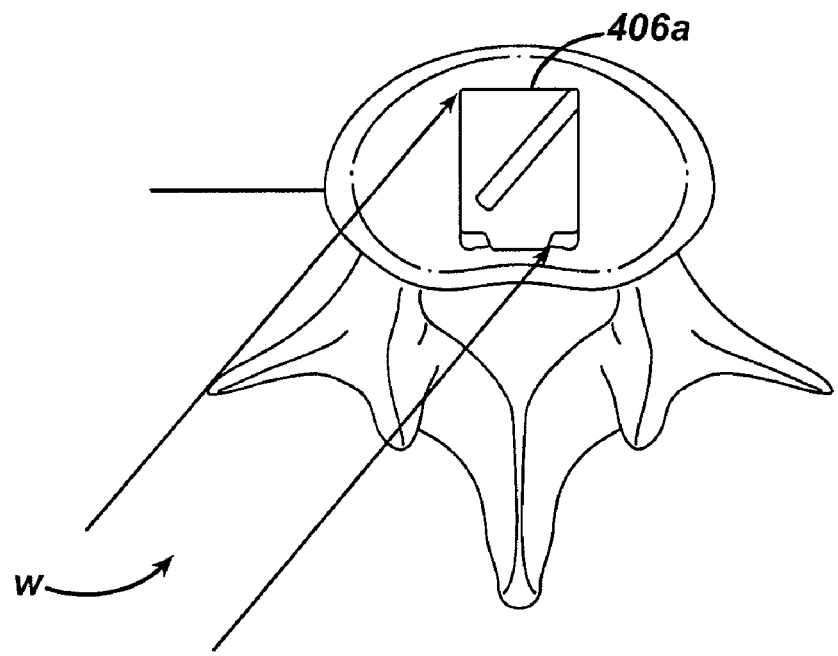
FIG. 4G is a top view of the superior and inferior central components of FIGS. 4C and 4D positioned on a vertebral body, showing a posterolateral surgical access window for introducing the central components.
Figure 4H:
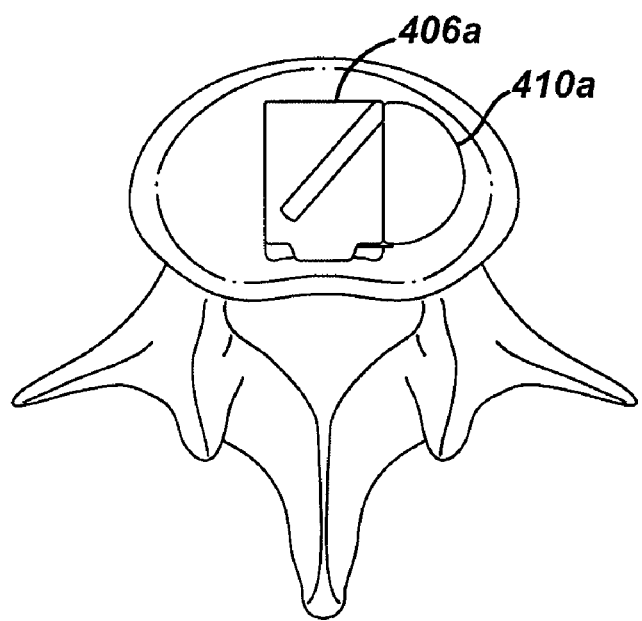
FIG. 4H is top view of the central components and vertebral body of FIG. 4G showing one of the superior and one of the inferior lateral components of FIGS. 4E and 4F mated to a first side of the central component.

FIGS. 4G-4H illustrate the implant in use. As shown in FIG. 4G, the central members (only superior member 406 is shown) of the implant 400 are introduced along an axis of a posterolateral surgical access window w to position the central component between the adjacent vertebra. As shown in FIG. 4F, the right superior and inferior lateral members (only superior member 410a is shown) is introduced using a posterior approach to mate the lateral members to the central members. The left superior and inferior lateral members 408a, 408b (not shown) can then be introduced on the contralateral side of the vertebra using a posterior approach to mate the left lateral members to the opposed side of the central members 406a, 406b. When mated, the central members 406a, 406b and the lateral members 408a, 408b, 410a, 410b form an implant having a footprint that is substantially equal to a footprint of a vertebral endplate, i.e., the implant is substantially disc-shaped to increase contact with the endplates of the adjacent vertebrae.

Figure 5A:
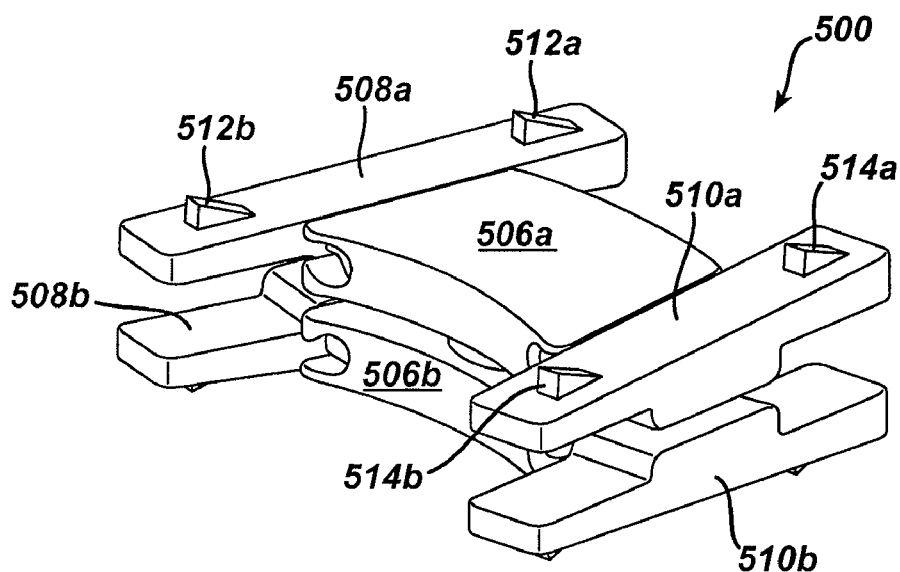
FIG. 5A is a perspective view of one exemplary embodiment of an implant that is configured to be inserted between adjacent vertebrae along a curved path using a posterolateral approach.
Figure 5B:
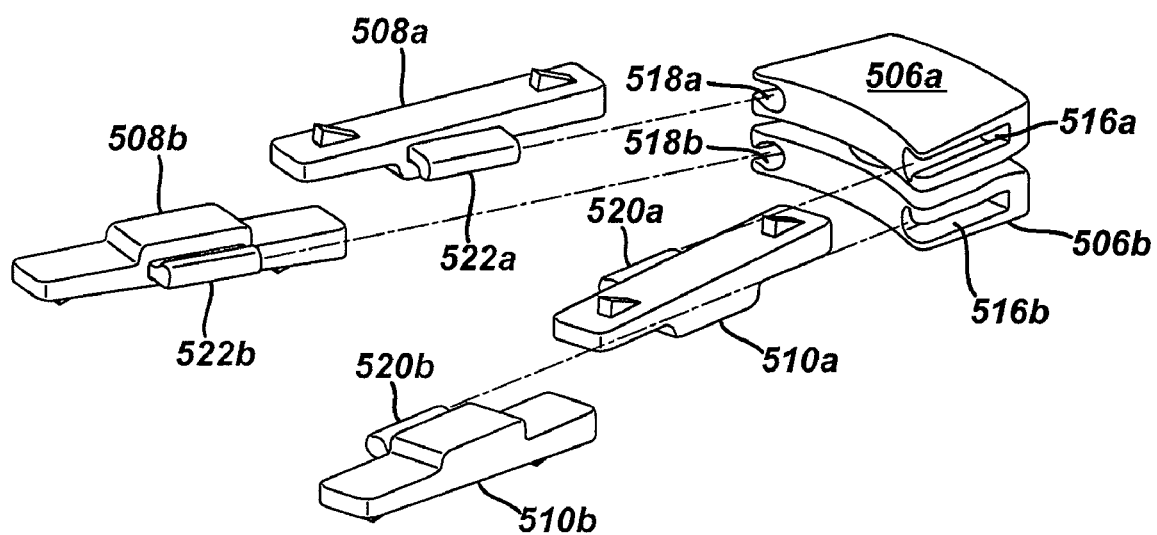
FIG. 5B is an exploded perspective view of the implant shown in FIG. 5A.

FIGS. 5A-5B illustrate another embodiment of an implant having a central component and left and right lateral components. In this embodiment, the central component of the implant 500 is substantially banana shaped and configured to be rotated once it is introduced into the disc space using a posterolateral approach. In particular, the central component includes superior and inferior central members 506a, 506b, which are shown in more detail in FIGS. 5C and 5D, respectively, that have a banana shape with curved posterior and anterior edges 518, 520, 522, 514, and lateral edges 530, 532, 534, 536 extending between the posterior and anterior edges 518, 520, 522, 514. The maximum width $w_5$ extending between the posterior and anterior edges 518, 520, 522, 514 of each member 506a, 506b is sized to allow the implant 500 to be introduced through a posterolateral access window without distracting nerves and dural elements with lateral edges 530, 536 leading, or with lateral edges 532, 534 leading. By way of non-limiting example, the maximum width $w_5$ can be about 13 mm. As the central members 506a, 506b approach or are within the disc space, the central members 506a, 506b can be turned to position the anterior edges 520, 514 adjacent to the anterior side of the disc space, and to position the posterior edges 518, 522 adjacent to the posterior side of the disc space. The curved configured can facilitate rotation of the central members 506a, 506b, however a person skilled in the art will appreciate that the central members 506a, 506b can have straight edges, or any other configuration that allows it to be introduced in a first orientation, and to be rotated into a second orientation within the disc space.

Figure 5C:
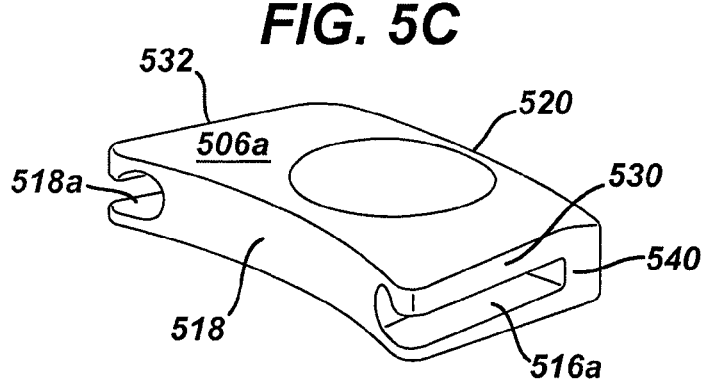
FIG. 5C is a perspective view of a superior central component of the implant shown in FIGS. 5A-5B.
Figure 5D:
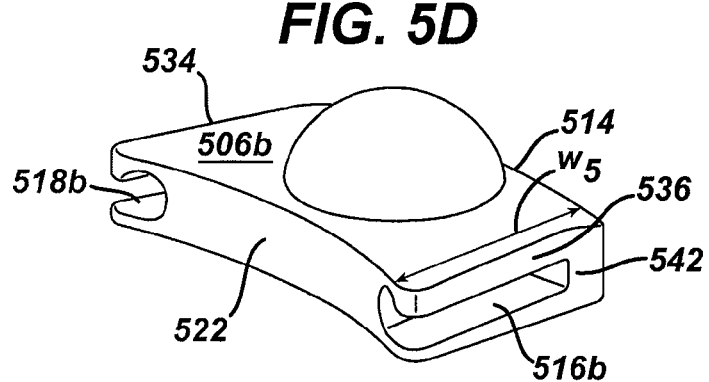
FIG. 5D is a perspective view of an inferior central component of the implant shown in FIGS. 5A-5B.
Figure 5E:
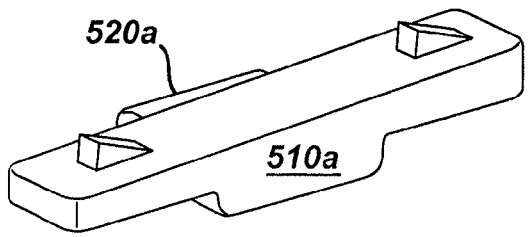
FIG. 5E is a perspective view of a superior lateral component of the implant shown in FIGS. 5A-5B.
Figure 5F:
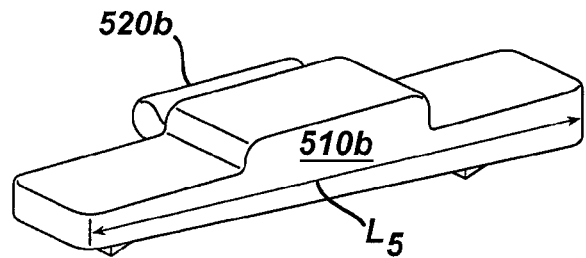
FIG. 5F is a perspective view of an inferior lateral component of the implant shown in FIGS. 5A-5B.

Once the central members 506a, 506b are implanted in the disc space and positioned properly, the left and right lateral components can be attached to the lateral edges 530, 532, 534, 536 of the central members 506a, 506b. A superior lateral member 510a is shown in FIG. 5E, and an inferior lateral member 510b is shown in FIG. 5F. As shown, each lateral member 510a, 510b has a generally elongate, rectangular configuration with a length $L_5$ that is greater than a width $w_5$ of the central members 506a, 506b. This allows the lateral members 508a, 508b, 510a, 510b to provide additional contact between the implant and the endplates of the adjacent vertebrae. The lateral members 508a, 508b, 510a, 510b can also help stabilize the central members 506a, 506b. In order to mate the lateral members 508a, 508b, 510a, 510b to the central members 506a, 506b, FIGS. 5A-5F illustrate grooves 516a, 516b, 518a, 518b formed on or within the central members 506a, 506b and complementary tongues 520a, 520b, 522a, 522b disposed on the lateral members 508a, 508b, 510a, 510b, similar to those described above in relation to FIGS. 4A-4F, for mating the components. FIGS. 5C and 5D also illustrated a stop surface 540, 542 formed at a terminal end of each groove 516a, 516b for preventing the lateral members 508a, 508b, 510a, 510b for sliding past the central members 506a, 506b. The stop surface can be formed by merely terminating the grooves 516a, 516b prior to the anterior edge 520, 514 of the central members 506a, 506b. A person skilled in the art will appreciate that other mating techniques can be used.

The implant can also include other features, such as keels 512a, 512b, 514a, 514b formed on the lateral members 508a, 508b, 510a, 510b. The keels can facilitate insertion of the lateral members, and they can also optionally function as bone-engaging surface features to mate the lateral members to the endplates of the adjacent vertebrae. While not shown, the central members 506a, 506b can also include keels or other features to facilitate insertion and implantation thereof.

Figure 6:
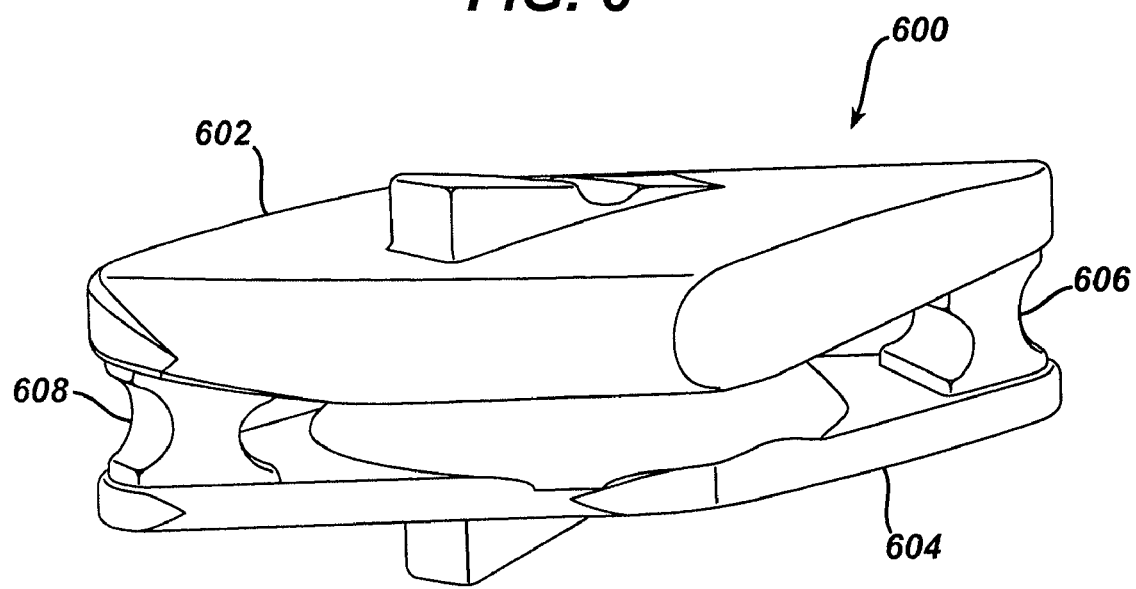
FIG. 6 is a perspective view of yet another exemplary embodiment of an implant that can be introduced between adjacent vertebrae using a posterolateral approach, showing struts extending between superior and inferior members of the implant to provide rotational control during movement of adjacent vertebrae.

In other embodiments, the various implants disclosed herein can include features to provide rotational control during movement of the adjacent vertebrae. For example, an elastomer structure, compressible element, spring, or other member can extend between and couple to the various superior and inferior members of the implant. By way of non-limiting example, FIG. 6 illustrates one embodiment of an implant 600 that is similar to the implant of FIGS. 1A-1B, but that includes first and second elastomer struts 606, 608 that extend between the articular surfaces of the superior and inferior members 602, 604. The struts 606, 608 can be positioned at any location, but they are preferably positioned on opposite sides of the implant 600 to provide uniform rotational control of the adjacent vertebrae. As shown in FIG. 6, the first strut 606 is positioned adjacent to the leading end of the implant, and the second strut 608 is positioned adjacent to the trailing end of the implant. The struts 606, 608 can be formed integrally with the superior and inferior members 602, 604, or they can be bonded to the superior and inferior members 602, 604 using various mating techniques known in the art. In other embodiments, the strut(s) can be removably mated to the implant to allow insertion of the members individually. Where the implant includes one or more lateral components, the struts can be formed or disposed between the superior and inferior lateral members. The embodiment previously shown in FIGS. 3A-3C illustrates a strut 312 which extends between the superior and inferior lateral members 308a, 308b. The strut 312 is positioned at a location opposite to the mating elements on the lateral members 308a, 308b.

Figure 7A:
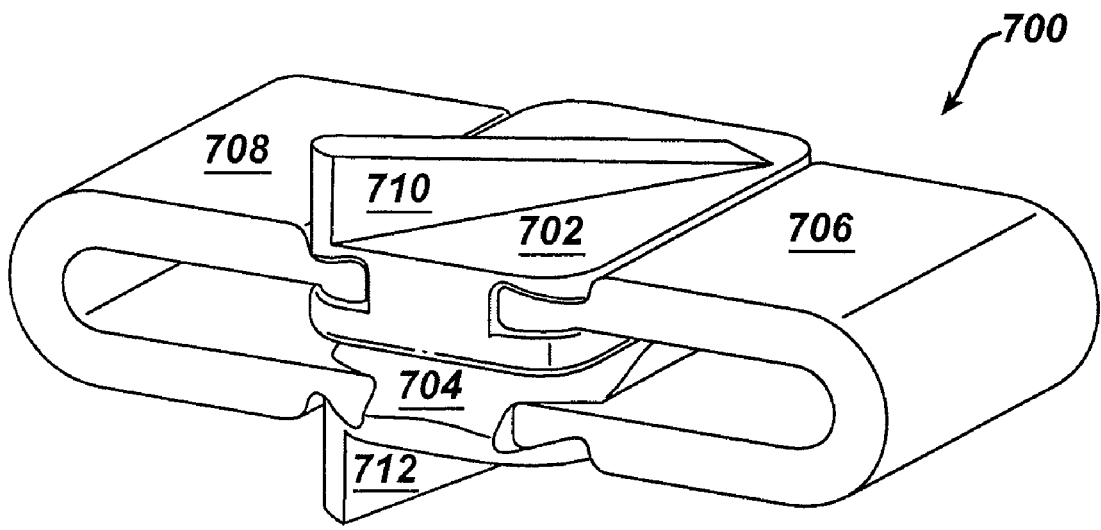
FIG. 7A is a perspective view of one exemplary embodiment of an implant having a central component that can introduced between adjacent vertebrae using a posterolateral approach and having lateral components in the form of springs that mate to the central component.
Figure 7B:
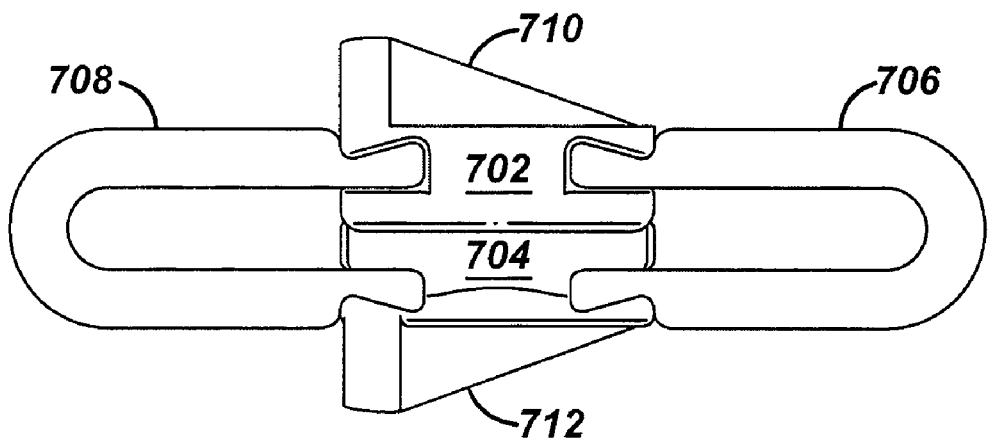
FIG. 7B is a side view of the implant shown in FIG. 7A.

FIGS. 7A and 7B illustrate another embodiment of a technique for providing rotational control. In this embodiment, the implant 700 includes superior and inferior central members 702, 704 similar to those described above in relation to FIGS. 4A-4F, and first and second lateral components 706, 708 that are in the form of springs. In particular, each lateral components 706, 708 is substantially U-shaped and includes terminal ends that slidably mate to the superior and inferior central members 702, 704. While various mating techniques can be used, FIGS. 7A-7B, illustrates a tongue-and-groove mating connection. In use, the lateral components 706, 708 can provide rotational control as the central members 702, 704 articulate relative to one another in coordination with movement of the adjacent vertebrae.

A person skilled in the art will appreciate that the implants disclosed herein can have a variety of other configurations. For example, a separate insert, such as a floating core, can be inserted between the central members to allow movement therebetween. Alternatively, the implant or central component of the implant can be formed from a single, unitary member that either allows, limits, or prevents movement between adjacent vertebrae. The lateral component(s) can likewise be formed from a single unitary member that merely mates to the central component to maximize contact with the endplates of the adjacent vertebrae.

The present invention also provides method for replacing a spinal disc. In an exemplary embodiment, an incision is made at a posterolateral location in a patient' back. A pathway is formed to the disc space by removing the facet joints, posterolateral annulus, and posterior lip, while leaving the remaining annulus and the anterior and posterior longitudinal ligaments in tact. The adjacent vertebrae are distracted, preferably on the contra-lateral side of the spine, and a discectomy is performed to remove the disc. The endplates can be prepared using various techniques known in the art. Where the implant includes a keel, grooves can be formed in the endplates to receive the keels therein. Once the disc space and endplates have been prepared, the implant or a component of the implant, e.g., the central component, can be introduced through the posterolateral access window. As previously explained, depending on the configuration of the implant, the implant can be introduced linearly along an axis of the access window, or it can curved once it is within the disc space to position it properly. Where the implant includes one or more lateral components, each lateral component can be introduced, preferably using a posterior approach, whereby the lateral components are inserted along an axis that is substantially parallel to an axis of the spinous process. This is preferably done through a separate surgical access window formed on one or both sides of the spine.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An artificial disc replacement implant, comprising:
   a central component having a superior member adapted to be positioned adjacent to an endplate of a superior vertebra, and an inferior member adapted to be positioned adjacent to an endplate of an adjacent inferior vertebra, the superior and inferior members being movable relative to one another, the central component further including leading and trailing ends and opposed first and second lateral sides extending between the leading and trailing ends, at least one of the lateral sides including a mating element formed thereon; and
   at least one lateral component extending laterally outward from at least one of the first and second lateral sides of the central component, the at least one lateral component having a mating element extending laterally-outward from a lateral edge of the lateral component and being slidably and removably matable to the mating element on at least one of the first and second lateral sides of the central component, and an elastic element that is configured to provide rotational resistance to adjacent superior and inferior vertebrae having the implant positioned therebetween.

2. The implant of claim 1, wherein the central component and the at least one lateral component have a superior and inferior footprint, when mated, that is substantially equal to a superior and inferior footprint of superior and inferior vertebrae between which the implant is adapted to be positioned.

3. The implant of claim 1, wherein the superior and inferior members each include a bone-contacting surface adapted to be positioned adjacent to bone, and an opposed articulating surface, the articulating surfaces being configured to move relative to one another to allow movement between the superior and inferior members.

4. The implant of claim 3, wherein the articulating surface on one of the superior and inferior members includes a concave cavity formed therein, and the articulating surface on the other one of the superior and inferior members includes a convex protrusion formed thereon and adapted to be received within the concave cavity.

5. The implant of claim 1, wherein the at least one lateral component is substantially U-shaped to form a spring.

6. The implant of claim 1, wherein the at least one lateral component includes a superior lateral member removably matable to the superior member of the central component, and inferior lateral member removably matable to the inferior member of the central component.

7. The implant of claim 6, wherein the superior and inferior lateral members are mated to one another by the elastic element which extends therebetween.

8. The implant of claim 1, wherein the at least one lateral component comprises a first lateral component having a superior lateral member and an inferior lateral member, and a second lateral component having a superior lateral member and an inferior lateral member, the first lateral component being removably matable to the first lateral side of the central component, and the second lateral component being removably matable to the second lateral side of the central component.

9. The implant of claim 1, further comprising a keel formed on at least one of the superior and inferior members and extending between the leading and trailing ends.

10. The implant of claim 9, wherein the keel has a height that increases from the leading end to the trailing end.

11. The implant of claim 9, wherein the keel extends substantially parallel to the opposed lateral sides.

12. The implant of claim 1, wherein the mating element on the at least one lateral component and the mating element on at least one of the first and second lateral sides of the central component comprises a tongue-and-groove.

13. A method for implanting a disc replacement, comprising:
   inserting a central component along an axis extending in a posterior-lateral direction into a disc space formed between adjacent vertebrae;
   inserting at least one lateral component along an axis extending in a posterior-anterior direction into the disc space, the central component and the at least one lateral component being inserted through different incisions; and
   coupling the at least one lateral component to at least one mating element formed on at least one lateral edge of the central component.

14. The method of claim 13, wherein the central component includes superior and inferior members that are movable relative to one another to allow movement of the adjacent vertebrae.

15. The method of claim 14, wherein the at least one lateral component includes superior and inferior members that are movably coupled to one another and that restrict rotation of the implant when the at least one lateral component is mated to the central component.

16. The method of claim 13, wherein inserting at least one lateral component comprises inserting a first lateral component along a first axis extending in a posterior-anterior direction into the disc space to couple the first lateral component to a mating element formed on a first lateral side of the central component, and inserting a second lateral component along a second axis extending in a posterior-anterior direction into the disc space to couple the second lateral component to a mating element formed on a second, opposed lateral side of the central component.

17. The method of claim 13, wherein the central component includes a keel formed on at least one of a superior and inferior surface thereof, and wherein the keel is aligned with the axis extending into the disc space.

18. The method of claim 13, wherein the central component includes a marker formed thereon, and wherein the method further comprises imaging the marker to determine a position of the central component relative to the adjacent superior and inferior vertebrae.

19. The method of claim 18, wherein the marker is selected from the group consisting of a cut-out formed in the keel, a radiopaque marker, and a radiolucent marker.

20. The method of claim 13, further comprising, prior to inserting, forming a surgical access window that extends from an incision formed in a patient's skin at a location posterior-lateral to the patient's spinal column to a disc space formed between adjacent superior and inferior vertebrae, and removing a disc disposed within the disc space.

21. The method of claim 20, wherein forming the surgical access window includes removing at least a portion of the facet joint extending between the adjacent superior and inferior vertebrae.

22. The method of claim 13, further comprising distracting the adjacent superior and inferior vertebrae from a contralateral side prior to inserting the central component.

* * * * *

UNITED STATES PATENT AND TRADEMARK OFFICE
CERTIFICATE OF CORRECTION

| | | |
|---|---|---|
| PATENT NO. | : 8,137,404 B2 | Page 1 of 1 |
| APPLICATION NO. | : 11/277725 | |
| DATED | : March 20, 2012 | |
| INVENTOR(S) | : Lopez et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 796 days.

Signed and Sealed this
Twenty-first Day of August, 2012

David J. Kappos
*Director of the United States Patent and Trademark Office*